United States Patent [19]

Adams

[11] Patent Number: 4,704,456

[45] Date of Patent: Nov. 3, 1987

[54] PROCESS FOR SULTAMICILLIN INTERMEDIATE

[75] Inventor: Richard C. Adams, Edgewater, Md.

[73] Assignee: Pfizer Inc., New York, N.Y.

[21] Appl. No.: 801,026

[22] Filed: Nov. 22, 1985

[51] Int. Cl.$^4$ .......................................... C07D 499/08
[52] U.S. Cl. .................................................. 540/310
[58] Field of Search ................ 540/310; 514/192, 195

[56] References Cited

U.S. PATENT DOCUMENTS 4,381,263  4/1983  Jasys ................................ 260/239.1

FOREIGN PATENT DOCUMENTS 2137193  10/1984  United Kingdom .

OTHER PUBLICATIONS

Binderup et al., Synthetic Communications, vol. 14, pp. 857–864 (1984).

*Primary Examiner*—Nicholas S. Rizzo
*Attorney, Agent, or Firm*—Peter C. Richardson; Albert E. Frost; Robert K. Blackwood

[57] ABSTRACT

An improved process for the preparation of the chloromethyl ester of sulbactam (chloromethyl penicillanate 1,1-dioxide), an intermediate in the synthesis of sultamicillin (the mixed methanediol ester of sulbactam and ampicillin).

12 Claims, No Drawings

PROCESS FOR SULTAMICILLIN INTERMEDIATE

Background of the Invention

The present invention is concerned with an improved method of preparing the chloromethyl ester of sulbactam

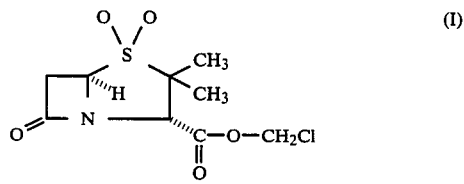

a key intermediate in the manufacture of sultamicillin. See Bigham, U.S. Pat. Nos. 4,244,951 and Godfredsen et al., 4,342,772. Sulbactam and sultamicillin are the U.S.A.N. (U.S. Adopted Names) or generic names for penicillanic acid 1,1-dioxide and for the mixed methandiol ester with sulbactam/ampicillin, respectively.

The preparation of the ester intermediate of the formula (I) in high yield and quality from the carboxylate ion

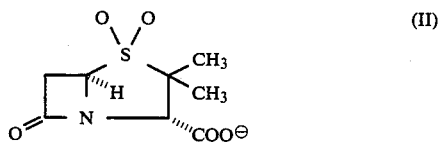

and chloroiiodome or chlorobromomethane has been generally frustrated by the formation of relatively large amounts of the bis-ester of the formula

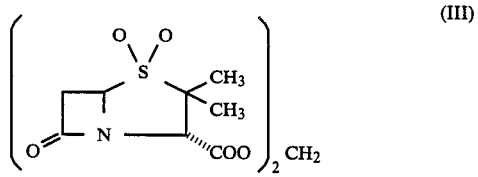

The use of tetrabutylammonium salt of the carboxylate (II) by Jasys, U.S. Pat. No. 4,381,263, improved the yield of the desired ester (I), but even here appreciable bis-ester (III) was formed [Binderup et al. Synthetic Communications, vol. 14, pages 857–864 (1984)].

More recently, Binderup et al. have employed chloromethyl chlorosulfate in place of chlorobromomethane or chloroiodomethane in reaction with the tetrabutylammonium salt of (II). Although the level of bis-ester is reduced thereby, the manifest toxicity of chloromethyl chlorosulfate (containing possible traces of even more toxic bis-chloromethyl ether) renders this process undesirable for plant scale operations.

SUMMARY OF THE INVENTION

In spite of the fact that the reactions of chloroiodomethane and bromochloromethane produce no acid entities when reacted with the tetrabutylammonium salt of (II), we have now discovered that in these reactions the addition of tert-amines and certain other substances such as acetylacetone, which might be deemed to be proton acceptors, surprisingly and unexpectedly further improves the yield of the desired monoester (I) at the expense of bis-ester (II). Just as surprising is the fact that the desired compound (I) is formed at a more rapid rate under these improved conditions, further enhancing plant productivity and so reducing costs.

DETAILED DESCRIPTION OF THE INVENTION

Essentially, the prior conditions of Jasys, cited above, are employed in the process of the present invention, but now in the presence of an additive which is a tertiary amine or a beta-diketone. Since the product is formed relatively cleanly in the reaction under the present conditions, it is readily isolated in a state of purity directly usable in the next step of the synthesis of sultamicillin, avoiding, for example chromatographic separation as employed by Jasys. The level of additive is not critical, but will generally be in the range of 0.1 to 1 molar equivalents. Temperature is not critical, but is conveniently ambient temperature. In view of the light sensitivity of chlorobromomethane and chloroiodomethane, it is preferred to run the reaction in the absence of light.

The preferred additives are tertiary amines particularly triethylamine, N-methylmorpholine, and most particularly, pyridine and N-(ethyl)diisopropylamine. Due to cost, stability and better recoverability, chlorobromomethane is preferred over chloroiodomethane.

Since the starting material (sulbactam; penicillanic acid 1,1-dioxide) is readily and separately recoverable from the reaction mixture, it is not necessary to carry the present reaction to completion. Such recovered starting material can, of course, be recycled in the preparation of further batches of the chloromethyl ester (I). Operation of the process in this manner can offer the advantage of employing reduced volumes of chlorobromomethane or chloroiodomethane, while at the same time producing directly recoverable monoester (I) containing levels of bis-ester (III) sufficiently low for further processing to sultamicillin. In any case, the excess chlorobromomethane or chloroiodomethane usually employed is preferably recovered for use in the preparation of further batches of monoester (I).

The present reaction is generally carried out in an excess of chlorobromomethane or chloroiodomethane, optionally diluted with a reaction-inert, preferably water-immiscible solvent, such as methylene chloride or ethyl acetate. The sulbactam starting material is readily recovered from such reaction mixtures by simple extration with water. The latter can be recovered as the tetrabutylammonium salt by stripping or freeze-drying, or in its free acid or an alternate form by standard methods of acidification, extraction and precipitation. Alternatively, the tetrabutylammonium salt is simply salted (e.g. with $Na_2SO_4$) back into fresh chlorobromomethane or chloroiodomethane and further reacted to form desired product.

As used herein, the expression "reaction inert solvent" refers to those solvents which do not interact with starting materials, intermediates or products in a manner which adversely affects the yield of the desired product.

Following removal of sulbactam starting material from the reaction mixture, the latter is equilibrated with aqueous sodium sulfate to convert by-product tetrabutylammonium bromide or iodide into its water soluble and now water extractable sulfate salt. Most of the excess chlorobromomethane or chloroiodomethane is then recovered by distillation from the reaction mixture. Crystalline sulbactam chloromethyl ester (I) is conveniently recovered by replacement of the residual concentrate with isopropyl alcohol (followed by cooling) or with ethyl acetate (followed by cooling and dilution with hexane). By-product bis-ester, which is generally found as a contaminant of desired monoester, does not interfere with subsequent processing to sultamicillin when its level is kept low, e.g., a weight % less than 10% (preferably less than 7.5% or lower) of the solids isolated. As already noted above, particularly at the higher concentrations generally preferred for plant scale processing, said low levels of bis-ester are best achieved by working up the reaction before complete reaction of the starting material, with recovery and recycling of same in the next batch.

The present invention is illustrated by the following examples. However, it should be understood that the invention is not limited to the specific details of these examples.

EXAMPLE 1

Sulbactam Chloromethyl Ester (Chloromethyl Penicillanate 1,1-Dioxide)

Tetrabutylammonium hydrogen sulfate (16.6 g, 0.049 mol) was dissolved in 100 ml of water with stirring at ambient temperature. The pH was adjusted from 1 to 7 with 2N NaOH. Sodium penicillanate 1,1-dioxide (10 g, 0.039 mol) was then added and the pH readjusted to 6.9 with 2N NaOH. $CH_2Cl_2$ (150ml) was added, the mixture stirred 10 minutes, the layers separated, and the aqueous layer washed with 150 ml of fresh $CH_2Cl_2$. The organic layers were combined, dried over $MgSO_4$ and stripped to yield tetrabutylammonium penicillanate 1,1-dioxide as an oil, pumped dry under high vacuum, 23.1 g, assumed to contain 18.6 g (a quantitative yield) of the tetrabutylammonium salt of penicillanic acid 1,1-dioxide. The entire batch was dissolved in 640 ml of chlorobromomethane containing pyridine (1.5 ml, 0.0186 mol). After 3.5 hours of stirring in the dark, the reaction mixture was washed in sequence with $2 \times 300$ ml $H_2O$, $1 \times 300$ ml saturated $Na_2SO_4$, $1 \times 300$ ml $H_2O$, and $1 \times 300$ ml saturated brine, dried over $MgSO_4$, decolorized with 3 g of activated carbon, and filtered over diatomaceous earth with 300 ml of ethyl acetate wash. The combined filtrate and wash was stripped to 50 ml, then displaced with a further 200 ml of ethyl acetate to a final volume of 25 ml. On stirring at room temperature, crystallization of the desired product began. On cooling to 0°-5° C., a thick slurry resulted. The latter was diluted dropwise with 50 ml of hexane and filtered with hexane wash to yield title product, 10.2 g (93%); assayed as 85% pure by hplc; containing about 7% by weight of bis-ester by hplc; 79% yield corrected for purity; purity suitable for further processing to sultamicillin.

This procedure was repeated except to use twice the volume (1280 ml) of $BrCH_2Cl$. There resulted 9.1 g (83%) of title product which assayed 95.8% pure by hplc; thus, a 79.5% yield corrected for purity. The product contained 5.8% by weight of the bis-ester by hplc assay.

The present hplc assays for sulbactam chloromethyl ester and bis-ester by-product were carried out on C-18 reversed phase having a particle size of 10 micrometers using 3:1 (v/v) 0.2M sodium dihydrogen phosphate:acetonitrile with pH adjustment to 3.0 after mixing, an injection volume of 0.010 ml, concentrations of sulbactam chloromethyl ester and bis-ester of about 0.25 mg/ml and 0.10 mg/ml respectively, and a flow rate of about 2 ml/minute. Detection was by ultra-violet at 215 nanometers. The compounds were quantitated by area under the curve measurements against standard samples.

EXAMPLE 2

Sulbactam Chloromethyl Ester

Tetrabutylammonium hydrogen sulfate (33.3 g, 0.098 mol) was reacted with sulbactam sodium salt (20 g, 0.078 mol) according to the preceding Example (except to use 5% $NaHCO_3$ for pH adjustments) to form the quaternary salt, all of which was dissolved in 1.3 liters of $BrCH_2Cl$ containing pyridine (3 ml, 0.037 mol) and stirred in the dark at ambient temperature for 3.5 hours. The reaction mixture was extracted $3 \times 500$ ml $H_2O$. The first two extracts were combined, adjusted to pH 1.5 with 6N HCl, extracted $2 \times 300$ ml of ethyl acetate. The organic layers were combined, back washed $1 \times 150$ ml $H_2O$ and then 150 ml brine, and stripped to yield 2.1 g of ethyl acetate wet sulbactam, [alpha]$_D$177.3° indicated 71% purity, an 8% recovery of starting material, in its free acid form, suitable for recycling.

Meanwhile, the water extracted reaction mixture was equilibrated with 500 ml of saturated $Na_2SO_4$ to convert and extract by-product tetrabutylammonium bromide as the water soluble sulfate), washed with 500 ml saturated brine, dried over 100 g $MgSO_4$, filtered and the filtrate concentrated to 60 ml with recovery of 1160 ml of $BrCH_2Cl$. The $BrCH_2Cl$ in the concentrate was displaced with 150 ml ethyl acetate to a final volume of 50 ml, cooled to 0°-5° C., and stirred as the product crystallized. Hexane (100 ml) was added dropwise over 10 minutes, granulation at 0°-5° C. continued for 20 minutes, and the mixture filtered with hexane wash and the solids dried for 18 hours in vacuo to yield 19.8 g of title product suitable for further processing to sultamicillin; purity by hplc, 86.8%, a 78% yield corrected for assay. Hplc indicated that the product contained 6.9% by weight of the bis-ester.

The same procedure repeated, using a reaction time of 2.5 hours without pyridine, gave a 15% assay corrected recovery of sulbactam, with a 66% assay corrected yield of title product containing 6.6% by weight of the bis-ester.

EXAMPLE 3

Sulbactam Chloromethyl Ester

The tetrabutylammonium salt of sulbactam (53 g of an oil) was prepared from sulbactam sodium salt (20.0 g, 0.078 mol) and tetrabutylammonium hydrogen sulfate (33.2 g) according to the method of Example 1. The entire 53 g batch was taken into 1280 ml of chlorobromomethane containing 1.70 ml (0.0098 mol) of diisopropylethylamine. After 5 hours, the reaction mixture was extracted with $3 \times 100$ ml of water. By optical rotation assay, the first, second and third extracts contained 5.7%, 1.1% and 0.3% of recovered sulbactam. The organic layer was stripped to a volume of 300 ml, and the $BrCH_2Cl$ displaced with $2 \times 500$ ml of ethyl acetate to a final volume of 275 ml, diluted with 100 ml fresh ethyl acetate, extracted $1 \times 275$ ml $H_2O$, $1 \times 275$ ml saturated Na$_2$SO$_4$, 1×275 H$_2$O and 1×275 ml brine, dried over 20 g MgSO$_4$, stirred with 4 g of activated carbon for 30 minutes, and filtered over diatomaceous earth with 100 ml of ethyl acetate wash. The filtrate and wash liquor were combined, stripped to 100 ml, cooled to 0°-5° C., diluted dropwise with 90 ml of hexane, maintaining 0°-5° C. (leading to an oil), warmed back to ambient temperature (causing the oil to form crystals), diluted dropwise over 1.5 hours with 150 ml of additional hexane, cooled and granulated at 0°-5° C. for 1 hour, and title product recovered in two crops (the second following evaporation of the mother liquor and trituration with hexane), 13.8 g and 4.7 g, both melting at 89°-95° C., a yield of 84% uncorrected, a yield of 80% corrected for purity by hplc.

EXAMPLE 4

Sulbactam Chloromethyl Ester

Sodium penicillanate 1,1-dioxide (20 g, 0.078 mol) was converted to the CH$_2$Cl$_2$ wet tetrabutylammonium salt according to the method of Example 1, then taken up in 1265 ml of BrCH$_2$Cl containing 3 ml of pyridine. After stirring for 6 hours in the dark, the reaction mixture was washed 2×600 ml H$_2$O and then distilled at reduced pressure (pot temperature, 20°-25° C.) to recover 1153 ml of BrCH$_2$Cl and leave a 50 ml concentrate of product. Residual BrCH$_2$Cl was displaced with 3×125 ml ethyl acetate, reducing to a 50 ml volume each time and the volume then adjusted to 250 ml with fresh ethyl acetate. This was equilibrated with 125 ml of aqueous Na$_2$SO$_4$ (prepared from 25 g Na$_2$SO$_4$ and 113 ml H$_2$O), and the organic layer was separated, washed with 125 ml of brine, dried over MgSO$_4$, and the ethyl acetate displaced in vacuo continuously with isopropyl alcohol (1680 ml), maintaining a pot temperature of 23°-34° C. and a pot volume of 175-225 ml. The resulting slurry, stripped to a final volume of 180 ml, was cooled to 5° C., granulated for 16 hours and title product recovered by filtration, 16.2 g (assaying 91% desired product, a 67% corrected yield, and 8.6% bis-ester), suitable for further processing.

EXAMPLE 5

Sulbactam Chloromethyl Ester

Tetrabutylammonium hydrogen sulfate (81.5 g, 0.24 mol) was dissolved in 450 ml H$_2$O and the pH adjusted to 7.0 with NaHCO$_3$ (solid). Sulbactam sodium salt (51 g, 0.020 mol) was added with stirring, followed by 450 ml of CH$_2$Cl$_2$ and then 50 g Na$_2$SO$_4$. The aqueous phase was separated and extracted with 450 ml fresh CH$_2$Cl$_2$. The CH$_2$Cl$_2$ layers were combined, dried over MgSO$_4$ and filtered with CH$_2$Cl$_2$ wash. The final volume of the combined filtrate and washes was 900 ml, determined to contain 0.20 mol of the tetrabutylammonium salt of sulbactam, based on stripping an aliquot of the salt solution (90 ml, 0.020 mol) to yield 11.5 g of solids.

A second aliquot of the salt solution (90 ml, 0.020 mol) was diluted with CH$_2$Cl$_2$ (310 ml) and BrCH$_2$Cl (100 ml, 1.5 mol) and pyridine (0.8 ml) was then added and the mixture stirred for 40 hours, stripped, maintaining a constant volume of 500 ml by the portionwise addition of 500 ml ethyl acetate, washed 2×100 ml H$_2$O and then 1×100 ml brine, stripped to a low volume as solvent was displaced with 250 ml isopropanol, cooled to 0°-5° C., and title product, containing low levels of bis ester by tlc, recovered by filtration, 3.8 g (67%).

A third 90 ml aliquot was reacted in like manner, except that the pyridine was added 2 hours after dilution with CH$_2$Cl$_2$ and addition of BrCH$_2$Cl, resulting in the recovery of 5.1 g (91%) of title product of similar purity.

I claim:

1. An improved process for the preparation of the chloromethyl ester of sulbactam which comprises reacting the tetrabutylammonium salt of sulbactam with a molar excess of chlorobromomethane or chloroiodomethane in a solvent comprising said molar excess of chlorobromomethane or chloroiodomethane in the presence of 0.1 to 1.0 molar equivalents of a beta-diketone or a tertiary amine.

2. A process of claim 1 which employs chlorobromomethane as reactant and excess chlorobromomethane or excess chlorobromomethane and methylene chloride as solvent.

3. A process of claim 2 wherein the process is carried out in the presence of 0.1 to 1 molar equivalents of acetylacetone, triethylamine, N-methylmorpholine, diisopropylethylamine or pyridine in excess chlorobromomethane as solvent.

4. A process of claim 2 wherein the process is carried out in the presence of 0.1 to 1 molar equivalents of a tertiary amine.

5. The process of claim 4 wherein the tertiary amine is pyridine.

6. The process of claim 4 wherein the tertiary amine is diisopropylethylamine.

7. A process of claim 1 which comprises recovering unreacted sulbactam and excess chlorobromomethane or chloroiodomethane for recycling, and which is carried out in a manner which permits recovery of the chloromethyl ester of sulbactam containing no more than 10% by weight of the corresponding bis-ester.

8. A process of claim 7 which employs chlorobromomethane as reactant and excess chlorobromomethane or methylene chloride as solvent.

9. A process of claim 8 wherein the process is carried out in the presence of 0.1 to 1 molar equivalents of acetylacetone, triethylamine, N-methylmorpholine, diisopropylethylamine or pyridine in excess chlorobromomethane as solvent.

10. A process of claim 8 wherein the process is carried out in the presence of 0.1 to 1 molar equivalents of a tertiary amine.

11. The process of claim 10 wherein the tertiary amine is pyridine.

12. The process of claim 10 wherein the tertiary amine is diisopropylethylamine.

* * * * *